(12) United States Patent
Snell (10) Patent No.: US 6,978,181 B1
(45) Date of Patent: Dec. 20, 2005

(54) INTER-PROGRAMMER COMMUNICATION AMONG PROGRAMMERS OF IMPLANTABLE MEDICAL DEVICES

(75) Inventor: Jeffery D. Snell, Chatsworth, CA (US)

(73) Assignee: Pacesetter, Inc., Sylmar, CA (US)

( * ) Notice: Subject to any disclaimer, the term of this patent is extended or adjusted under 35 U.S.C. 154(b) by 608 days.

(21) Appl. No.: 10/155,475

(22) Filed: May 24, 2002

(51) Int. Cl.$^7$ ............................................. A61N 1/00
(52) U.S. Cl. ........................ 607/60; 607/30; 607/32; 607/2; 128/903
(58) Field of Search ............................... 607/2, 4–5, 9, 607/32, 57, 60, 30; 128/903–904, 899

(56) References Cited

U.S. PATENT DOCUMENTS

| | | | |
|---|---|---|---|
| 5,107,833 A | 4/1992 | Barsness | 607/32 |
| 5,415,181 A | 5/1995 | Hogrefe et al. | 600/549 |
| 5,683,432 A | 11/1997 | Goedeke et al. | 607/32 |
| 5,843,139 A | 12/1998 | Goedeke et al. | 607/32 |
| 6,115,628 A | 9/2000 | Stadler et al. | 600/517 |
| 6,115,630 A | 9/2000 | Stadler et al. | 600/521 |
| 6,128,526 A | 10/2000 | Stadler et al. | 600/517 |
| 6,167,312 A | 12/2000 | Goedeke | 607/60 |
| 6,169,925 B1 | 1/2001 | Villaseca et al. | 607/60 |
| 6,240,317 B1 | 5/2001 | Villaseca et al. | 607/60 |
| 6,249,703 B1 | 6/2001 | Stanton et al. | 607/30 |
| 6,249,705 B1 * | 6/2001 | Snell | 607/59 |
| 6,308,099 B1 * | 10/2001 | Fox et al. | 607/31 |
| 6,424,867 B1 * | 7/2002 | Snell et al. | 607/31 |
| 2001/0023360 A1 | 9/2001 | Nelson et al. | 607/60 |
| 2001/0031997 A1 | 10/2001 | Lee | 607/59 |
| 2001/0031998 A1 | 10/2001 | Nelson et al. | 607/60 |
| 2003/0171789 A1 * | 9/2003 | Malek et al. | 607/60 |

* cited by examiner

Primary Examiner—Carl Layno (57) ABSTRACT

A telemetry architecture is described that enables multiple programmers to concurrently interact with associated implantable medical devices within a viable telemetry range. The programmers communicate with implantable medical devices over one or more communication channels. Inter-programmer communication is accomplished over a particular communication channel that may be selected from one of the programmer-to-device channels or via an independent back channel. The programmers use the inter-programmer communication to coordinate communication between associated programmers and implantable medical devices within the viable telemetry range.

45 Claims, 9 Drawing Sheets

Fig. 9

INTER-PROGRAMMER COMMUNICATION AMONG PROGRAMMERS OF IMPLANTABLE MEDICAL DEVICES

TECHNICAL FIELD

The present invention generally relates to implantable medical devices, and particularly, telemetry architectures for enabling communication between a programmer and an implantable medical device when multiple programmers and/or multiple devices are present.

BACKGROUND

There are many kinds of implantable medical devices. Some monitor patient conditions while others disperse some form of therapy. One particular type of implantable medical device is an implantable cardiac therapy device, or ICTD. ICTDs are implanted within the body of a patient to monitor, regulate, and/or correct heart activity. ICTDs include implantable cardiac stimulation devices (e.g., implantable cardiac pacemakers, implantable defibrillators) that apply stimulation therapy to the heart as well as implantable cardiac monitors that monitor heart activity.

With advances in microelectronics, many implantable medical devices are miniature computers with memory and processing capabilities. Such devices are capable of being programmed remotely by an external programming device, often called a "programmer". An implanted device and a programmer communicate using wireless telemetry technologies. Early telemetry systems were passive, meaning that communication was unidirectional from the programmer to the implanted device. Passive telemetry allowed a treating physician to download instructions to the implanted device following implantation. Due to power and size constraints, early commercial versions of implanted devices were incapable of transmitting information back to the programmer.

As power capabilities improved, active telemetry became feasible. This allowed bi-directional communication between the implanted device and the programmer. With active telemetry, the treating physician is able to both program the implanted device and retrieve information from the implanted device to evaluate heart activity and device performance.

Current telemetry systems have limited communication range between the programmer wand and device. The programmer utilizes an electromagnetic wand that is placed within a few inches of the implanted cardiac device to communicate with the implanted device. The wand contains a coil that forms a transformer coupling with the telemetry circuitry in the device and low frequency signals are transmitted via the coupling. Due to the limited range, such telemetry systems are often referred to as "short-range telemetry" or "wand telemetry".

With advancements being made in telemetry technologies, the communication range is expected to increase beyond a few inches to several feet or more. An increased telemetry range will provide many advantages, including more mobility for the patient during telemetry and more flexibility in the positioning of the telemetry antenna. For example, increasing the range would allow a programmer to monitor, for example, a patient exercising on a treadmill, or moving around at home, or a patient that walks into a waiting room.

Unfortunately, an increased telemetry range does not come free of problems. One new problem introduced by longer-range telemetry is the potential of interference between separate programmers that are being used to program multiple devices within a common telemetry range. Traditionally, telemetry systems have employed a single communication channel, which enables a single programmer to communicate with a single implantable device. This was a reasonable approach given that the communication range was limited to a few inches. But, as the range increases, there is the potential for interference on that channel. This interference may be in either or both directions of the telemetry link between the programmer and the implantable device.

Accordingly, there is a need for a more comprehensive telemetry architecture that accommodates multiple programmers communicating with multiple implantable devices within a common communication range.

SUMMARY

A telemetry architecture is described that enables multiple programmers to concurrently interact with associated implantable medical devices within a viable telemetry range. The programmers communicate with implantable medical devices over one or more communication channels. Inter-programmer communication is accomplished over a particular communication channel that may be selected from one of the programmer-to-device channels or via an independent back channel. The programmers use the inter-programmer communication to coordinate communication between associated programmers and implantable medical devices within the viable telemetry range.

BRIEF DESCRIPTION OF THE DRAWINGS

In the description that follows, like numerals or reference designators are used to reference like parts or elements.

DETAILED DESCRIPTION

Architecture

Figure 1:
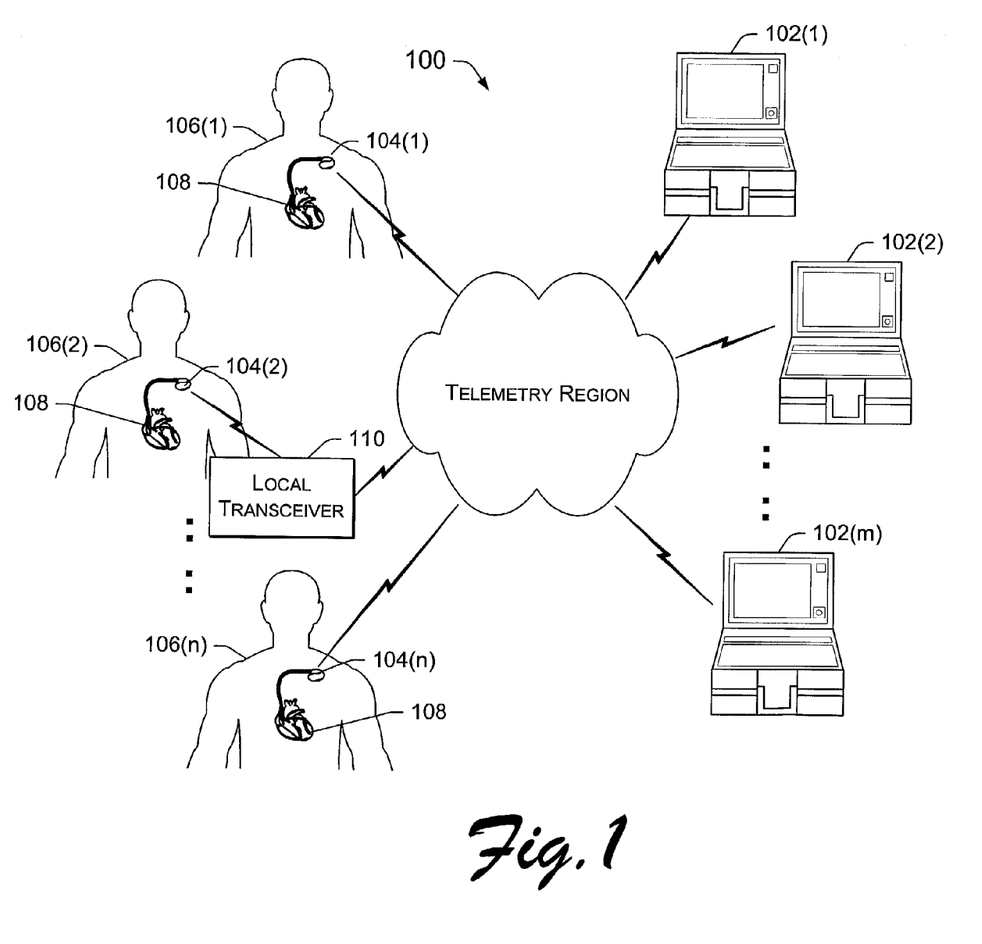
FIG. 1 is a diagrammatic illustration of a telemetry architecture that supports multiple programmers communicating with multiple implantable devices within a viable telemetry range.

FIG. 1 shows a telemetry architecture 100 in which multiple programmers 102(1), 102(2), . . . , **102(*m*) are capable of communicating with multiple implantable medical devices (104(1), 104(2), . . . , 104(n)) within a viable telemetry range. For discussion purposes, the implantable medical devices 104 are illustrated as implantable cardiac therapy devices (ICTDs) implanted in human patients 106 (1), 106(2), . . . , 106(n). Each ICTD is in electrical communication with the patient's heart 108** by way of multiple leads suitable for monitoring cardiac activity and/or delivering multi-chamber stimulation and shock therapy. It is noted that the ICTD is just one exemplary type of implantable medical device. Other types of implantable medical devices may be employed, such as implantable medicine dispensers, implantable nerve stimulators, implantable bio-monitoring devices, and so on. Such other devices may be in electrical communication with other anatomies of the patient.

Each programmer 102 is capable of communicating with an implantable medical device 104 for purposes of programming the device and/or gathering data from it. The programmers and implantable devices may use one or a combination of various wireless technologies to communicate with one another including wand-like transformer-based telemetry, radio frequency communication, cellular technologies, infrared technologies, Bluetooth, technologies conforming to IEEE 802.11, and so on.

The programmers 102 may communicate directly with an implantable device 104, or alternatively via an intermediary communicating device represented by local transceiver 110. Examples of an intermediary communicating device include a local coil-type telemetry unit, a personal digital assistant that is equipped with communication capabilities, a cellular phone, a computer, and so forth. A programmer 102 may be connected to the intermediary communicating device 110 via various network technologies, including both wireless technologies (e.g., RF, cellular, microwave, satellite, etc.) and wire-based technologies (e.g., LAN, cable, Internet, etc.), and optics-based technologies (e.g., fiber optics, infrared, etc.).

At least one communication link between a programmer 102 and an implantable device 104 is wireless. This gives rise to the possibility of interference among the multiple devices and programmers within the viable telemetry range. A viable telemetry range is one in which at least a subset of the programmers 102 and/or at least a subset of the implantable devices 104 are capable of communicating with one another within a shared or common transmission region. In this shared region, there is a possibility of overlapping or interfering communication. For example, two or more programmers may be within range to communicate with each other and/or with one or more implantable devices. Similarly, two or more implantable devices may be within range to communicate with each other and/or with one or more programmers.

This can be visualized as circles representing the telemetry range of each programmer and device—with the programmer or device at the center of each circle. The radius of the circle is the range of the telemetry of that device and the radii may not be uniform as the ranges of different devices may be different. If two of these circles are positioned so that the center of both circles falls within the radius of the other circle, these two devices can communicate because their respective telemetry ranges can reach the other party in the communication. If the radius of one circle reaches the center of another circle for a device it does not intend to communicate with, interference can occur if the same communication channels are in use by the devices in both circles. If several circles are all overlapping, then all of these devices have the potential to communicate and/or interfere with each other. Thus, interference can be caused by other programmers and/or other implantable devices that are not privy to the communication.

To avoid such interference, the programmers 102 and implantable devices 104 are configured to communicate over multiple channels. In this manner, a communicating pair of entities (e.g., programmer to implantable device, programmer to programmer, implantable device to implantable device) can establish a point-to-point communication link within the viable telemetry range by selecting and using one of the communication channels.

Additionally, the programmers 102 may be configured to coordinate their communication with individual implantable devices. The programmers may use in-channel or out-of-channel processes to facilitate non-interfering communication over one or more of the communication channels. In the event interference on any given channel does occur, the programmers 102 may also be equipped with an alarm to warn healthcare professionals of the interference.

Figure 2:
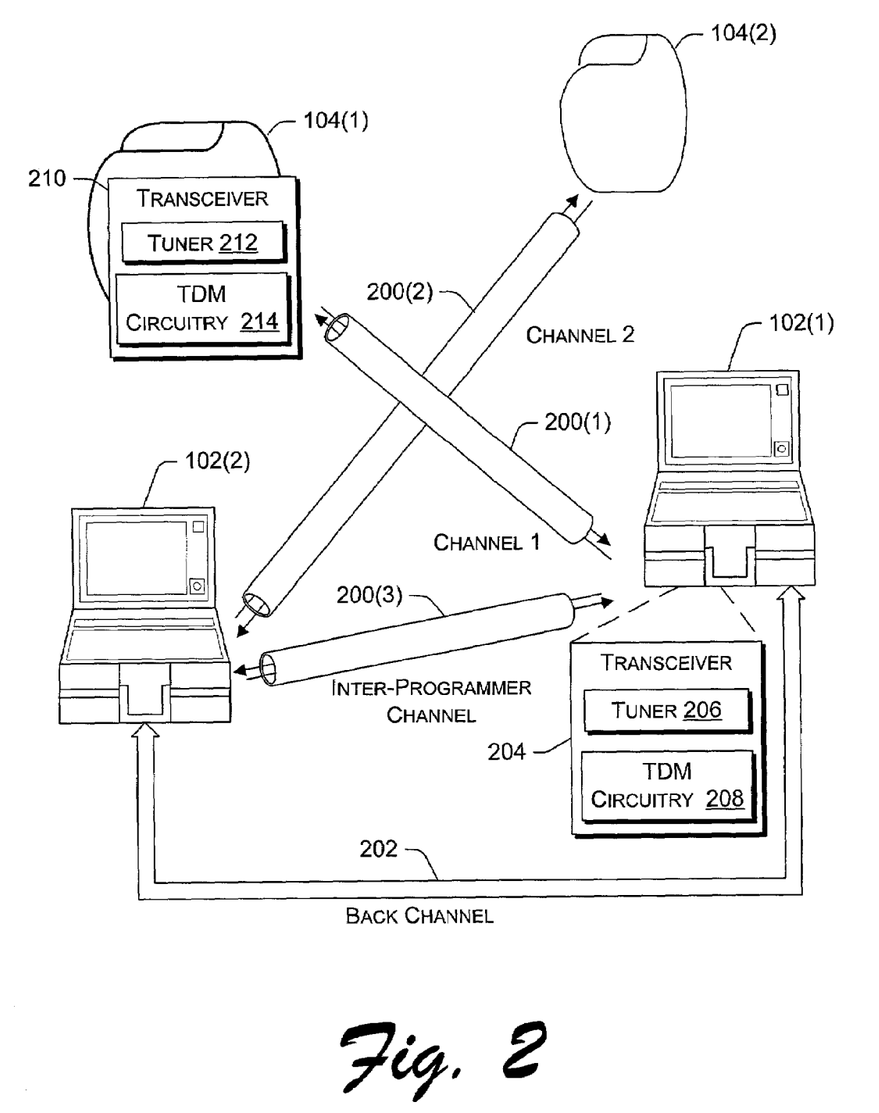
FIG. 2 illustrates multiple programmers and devices communicating over different channels.

FIG. 2 illustrates a multi-channel communication process to enable point-to-point communication between any pair of communicating entities in the viable telemetry range. Here, two programmers 102(1) and 102(2) establish communication links with implantable medical devices 104(1) and 104(2), respectively. Programmer 102(1) communicates with implantable device 104(1) via communication channel 200(1). Similarly, programmer 102(2) communicates with implantable device 104(2) via communication channel 200 (2). The programmers 102(1) and 102(2) may communicate with each other via a third communication channel 200(3). Each of the communication channels 200(1)–200(3) includes a wireless telemetry link.

The programmers may alternatively (or additionally) communicate through a back channel 202. This back channel may be established using wired technologies (e.g., Ethernet or other local area network technologies, the Internet, etc.) and/or wireless technologies that do not interfere with the telemetry channels (e.g., infrared link, etc.) For this implementation, the programmers are equipped with a network port that facilitates connection to the back channel 202. Thus, the programmers may function as standalone units, or as networked programmers that communicate with other programmers and/or backend computer servers.

Each programmer, as represented pictorially by programmer 102(1), is equipped with a transceiver 204 that is capable of sending and receiving signals over a wide range of frequencies, such as broadband RF signals. A tuner 206 is provided to tune to these different frequencies. With the transceiver 204 and tuner 206, the programmer 102 is able to employ spread spectrum techniques to channel hop among multiple frequencies. Each programmer may additionally, or alternatively, be configured with time division multiplexing (TDM) circuitry 208 to produce multiple time-divided channels on one frequency. Accordingly, the programmer 102 is capable of formulating and communicating over multiple channels by changing frequencies and/or changing time slots within a single frequency.

Each programmer may also be configured to store a table or other data structure (not shown) in memory for purposes of tracking whether certain telemetry channels are available or in use. For instance, the programmer marks channels that are currently being used by other programmers and devices as reserved. As these channels become free, the programmer mark them as available. This internal record keeping is one possible implementation that makes selecting an available channel more efficient.

Each implantable medical device, as represented by device 104(1), is equipped with a transceiver 210 that is capable of narrow or broadband communication. The device 104(1) may be further configured to include at least a tuner 212 to facilitate communication over multiple channels defined by different frequencies and/or TDM circuitry 214 to facilitate communication over multiple channels defined by different time slots on a single frequency.

The multiple channels allow multiple programmers and devices to communicate free of interference within a viable telemetry range. The communicating devices establish a point-to-point communication channel by choosing a free frequency or a free time slot. One exemplary multi-channel communication process is described below with reference to FIG. 4.

Another approach to combating interference from other programmers and/or implantable devices is to provide a protocol for signaling all devices to transition to a "listen only" mode. In this manner, if interference is hindering communications, the desired device can be addressed specifically and a communication conversation initiated. The programmers coordinate with one another to transmit a "listen only" command so that all devices in the viable telemetry range can be quieted. Afterward, a coordinated resumption of communication can begin, one conversation at a time, so that if two conversations are interfering they can be identified and coordinated appropriately through a variety of procedures (e.g., highest priority first, alternate sharing of the bandwidth, switch to a different non-interfering channel/slot, etc.).

Exemplary Programmer

Figure 3:
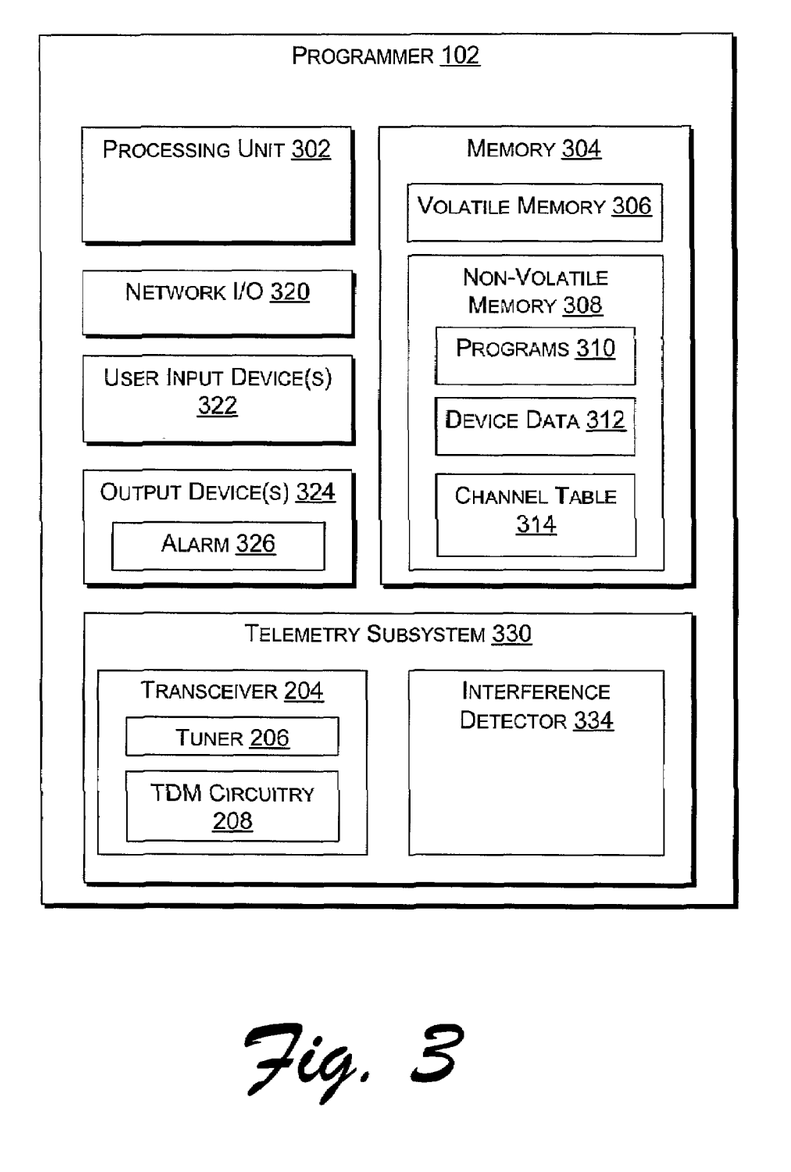
FIG. 3 is a functional block diagram of an exemplary programmer that is equipped with a telemetry subsystem for multi-channel communication and an alarm.

FIG. 3 shows an exemplary programmer 102 employed in the telemetry architecture 100. It includes a processing unit 302 and memory 304. The processing unit 302 controls operations carried out by the programmer 102, such as programming the implantable medical device, gathering data from the implantable device, and/or carrying out various testing or diagnostic functions. Memory 304 includes both volatile memory 306 (e.g., RAM) and non-volatile memory 308 (e.g., ROM, EEPROM, Flash, disk, optical discs, persistent storage, etc.).

Programs, operating parameters, and algorithms 310 that are used in controlling the programming and testing functions may be stored in memory 304. When a program is running, various instructions are loaded into volatile memory 306 and executed by processing unit 302. Device data 312 collected from the implantable device may be stored in the programmer memory 304 for subsequent analysis and/or transfer to other computing systems.

A channel table 314 may also be maintained in the non-volatile memory 308. This table lists the various channels that the programmer may use to communicate with tan implantable device. The table also tracks which of the channels are available for use and which are being used by other programmers. The programmers may coordinate among themselves to minimize interference and such channel-related information can be shared to keep the table 314 updated.

The programmer 102 may further be equipped with a network I/O connection 320 to facilitate communication with a network, which may be used to form the back channel 202. The network I/O 320 may be a wire-based connection (e.g., network card, modem, etc.) or a wireless connection (e.g., RF transceiver, Bluetooth device, etc.).

The programmer 102 may also include one or more user input device(s) 322 (e.g., keyboard, mouse, stylus, touch pad, touch screen, voice recognition system, etc.) and one or more output device(s) 324 (e.g., monitor, LCD, speaker, printer, dedicated storage systems, etc.). One output device implemented in the programmer 102 is an interference alarm 326 that is sounded when the programmer detects potential or actual interference on the channel being used to communicate with an implantable device.

The programmer 102 is equipped with a telemetry subsystem 330 to communicate with an implantable medical device. The telemetry subsystem 330 includes the transceiver 204, tuner 206, and/or TDM circuitry 208.

The telemetry subsystem 330 also has an interference detector 334 to detect actual or potential interference that might affect effective communication with the implantable device. The interference detector 334 listens on a particular channel during periods when the programmer is not communicating with the implantable device. If the interference detector 334 detects signals of sufficient energy (i.e., above a predetermined threshold level), it outputs a warning signal that is conveyed to the healthcare professional in the form of an audio sound emitted by alarm 326 and/or a visual warning displayed on the display.

The components illustrated in FIG. 3 are interconnected via one or more buses (not shown). Additionally, various aspects of the methods and systems described throughout this disclosure may be implemented in computer software or firmware as computer-executable instructions. When executed, these instructions direct the programmer (alone, or in contact with other programmers) to perform various functions and tasks that enable the architecture 100.

Multi-Channel Telemetry

Figure 4:
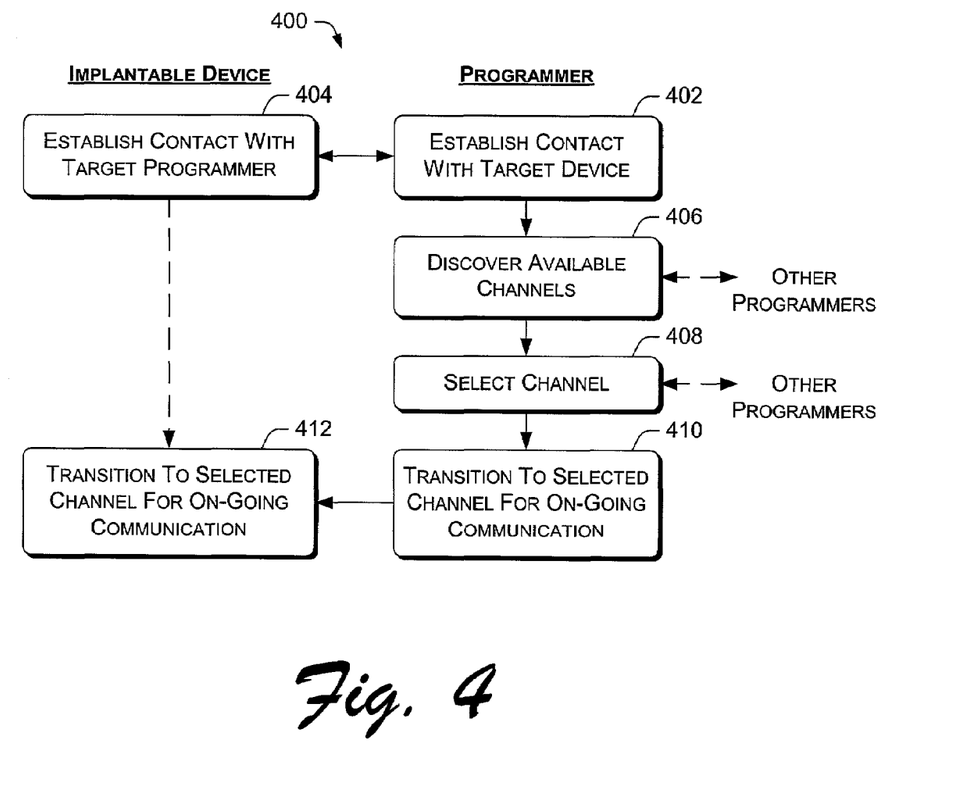
FIG. 4 is a flow diagram of a multi-channel communication process that enables point-to-point communication between any pair of participating entities in the viable telemetry range.

FIG. 4 shows a multi-channel communication process 400 for establishing a communication channel between a programmer 102 and an implantable device 104. Aspects of this process may be implemented in hardware, firmware, or software, or a combination thereof. The multi-channel communication process 400 is accomplished by operations performed at the device 104 and the programmer 102. To illustrate which devices perform which operations, the various operations are depicted as blocks arranged beneath headings identifying the devices that generally perform the operations.

At blocks 402 and 404, the programmer 102 and the device 104 establish contact with one another. This may be accomplished in a number of ways. One approach is for the programmer 102 to transmit interrogation messages on a pre-designated channel or frequency so that any listing device within range can respond. Another approach is to initiate communication for a particular device on a pre-arranged channel or frequency when that device is known to be within range. For instance, a healthcare professional can load a patient's record into the programmer and when that patient arrives, the professional can initiate a communication cycle between the programmer and the implantable device. The programmer uses information from the patient's record to ensure that it is communicating with the intended device. Yet another approach is to scan all the available channels polling for devices on each until one is found. Still another approach is to use a discovery protocol in which the devices within a viable telemetry range exchange identifies, credentials, and capabilities with one another.

At block 406, the programmer discovers what channels are available for communication. The discovery may be implemented in a number of ways. For instance, the programmer may scan available frequency ranges to see which ones are free. Another approach is for the programmer to communicate with other programmers via an open channel 200(3) or a back channel 202 to coordinate with them what frequency or time slot is available. This approach is discussed below in more detail. Still another approach is to have ranges of frequencies (for spread spectrum techniques) or specified time slots (for TDM techniques) assigned to various programmers within a viable telemetry range. In this manner, each programmer would be able to communicate with any one device within a channel limited by the frequency range or time slot.

At block 408, the programmer selects a communication channel for communicating with the target implantable device. Once selected, the programmer may wish to communicate this selection to other programmers in the event such programmers are coordinating their communication. At blocks 410 and 412, the programmer 102 and the device 104 use the selected channel for ongoing communication. The transition to that channel might entail tuning to a certain frequency or listening to a particular frequency for packages sent in a selected time slot. Once the channel is selected, the devices may employ cryptography technologies to further secure point-to-point communication.

The process 400 is described in the context of the programmer initiating communication. It should be noted that the implantable device may also be configured to initiate communication as soon as it enters the viable telemetry range.

Inter-Programmer Signaling

Figure 5:
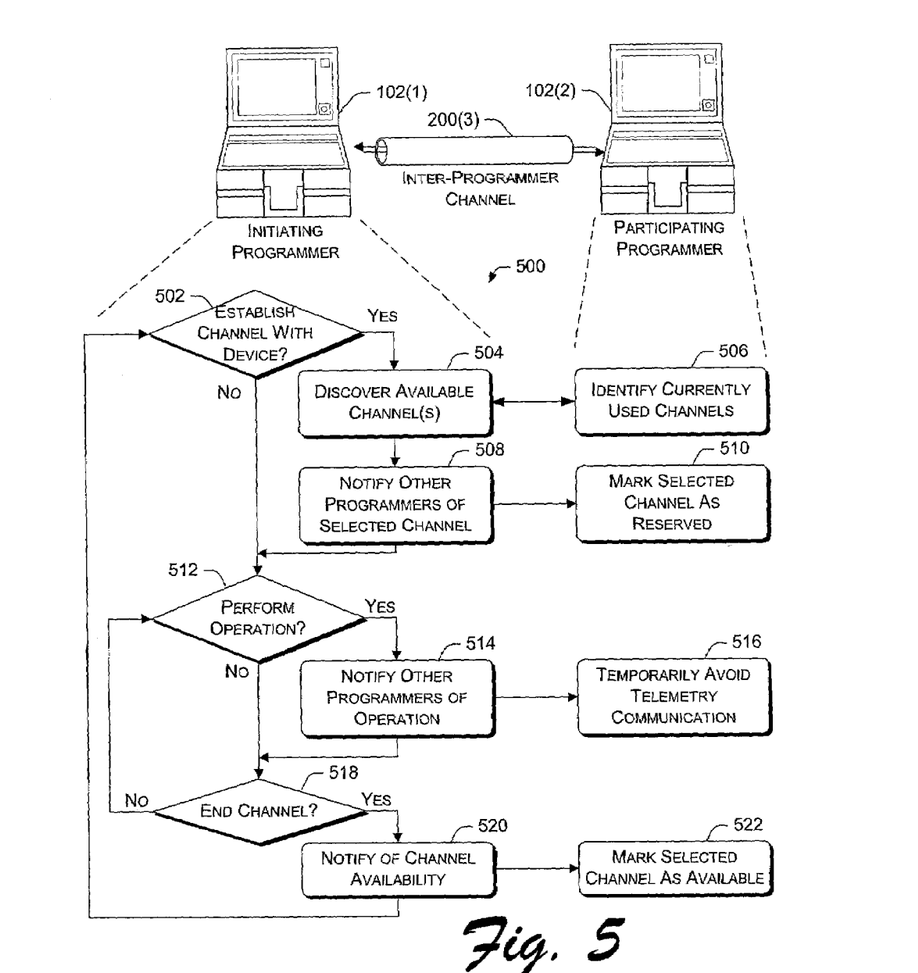
FIG. 5 illustrates a coordinated inter-programmed communication process that coordinates programmer communication with the implantable devices.

FIG. 5 shows a process 500 that is executed by individual programmers to facilitate inter-programmer communication. The programmers communicate with one another for purposes of coordinating their use by the telemetry channels designated for implantable devices. For discussion purposes, an initiating programmer 102(1) communicates with a participating programmer 102(2) over the telemetry channel 200(3). Using the inter-programmer telemetry channel 200 (3) introduces additional challenges to ensure that such communications do not interfere with programmer-to-device telemetry. It is noted, however, that aspects described in process 500 may be used to facilitate communication over the back channel 202.

At block 502, the programmer determines whether it wishes to establish communication with a particular implantable device. If so (i.e., the "yes" branch from block 502), the programmer communicates with other programmers that are, or might be, communicating with implantable devices within the viable telemetry range. At block 504, the programmer checks with the other programmers via the inter-programmer channel 200(3) to identify which telemetry channels within the viable telemetry range might be free and available for use. Each programmer knows which channel(s) it is currently using, if any, and is able to supply this information to the requesting programmer. At block 506, the participating programmer 102(2) returns any channels that it currently knows to be reserved or in use by another programmer. The initiating programmer takes this information and updates its channel table to reflect which channels are available.

At block 508, once the initiating the programmer 102(1) identifies a suitable channel, it notifies the other programmers via the inter-programmer channel 200(3) of the selected channel and its intention of using that channel for communication with an implantable device. At block 510, the participating programmer updates its own channel table to reflect that the selected channel is now reserved for use by the initiating programmer. From this point, the initiating programmer can communicate with the target device over the selected communication channel.

At operation 512, a determination is made as to whether the initiating programmer is performing an operation that warrants telling other programmers to minimize or avoid communication until the operation is performed. Such operations may be of a sensitive nature, such as programming a particular implantable device. In this case, the programmer might want to inform other programmers to stop communicating temporarily to ensure that transmission of programming parameters over the channel is free from any interference. Alternatively, the operations may simply be communications with the implantable device. In this manner, the programmers interact with one another to coordinate all of their communication with implantable devices so that each programmer-to-device communication is free from cross-talk or other forms of interference.

If an operation warrants such notice, the initiating programmer 102(1) notifies other programmers of the impeding operation via the inter-programmer channel 200(3) (block 514). At block 516, the participating programmer temporarily avoids communication on the designated channel (and perhaps any communication on any channel) until the temporary period has lapsed. An alternative approach is to signal all devices to transition to a "listen only" mode to temporarily halt communication. This allows the programmer to communicate directly with one intended device, while other programmers and/or devices wait without communicating.

At block 518, the initiating programmer determines whether it is done interacting with the implantable device and hence, ready to drop the communication channel. If the initiating programmer is not yet done (i.e., the "no" branch from block 518), the initiating programmer continues to perform other operations until it is done interacting with the implantable device. When the interaction is done, the initiating programmer 102(1) notifies other programmers via the inter-programmer channel 200(3) that the channel is now available and updates its channel table (block 520). In response, the participating programmer 102(2) updates its channel table to reflect that the channel is now available (block 522).

Figure 6:
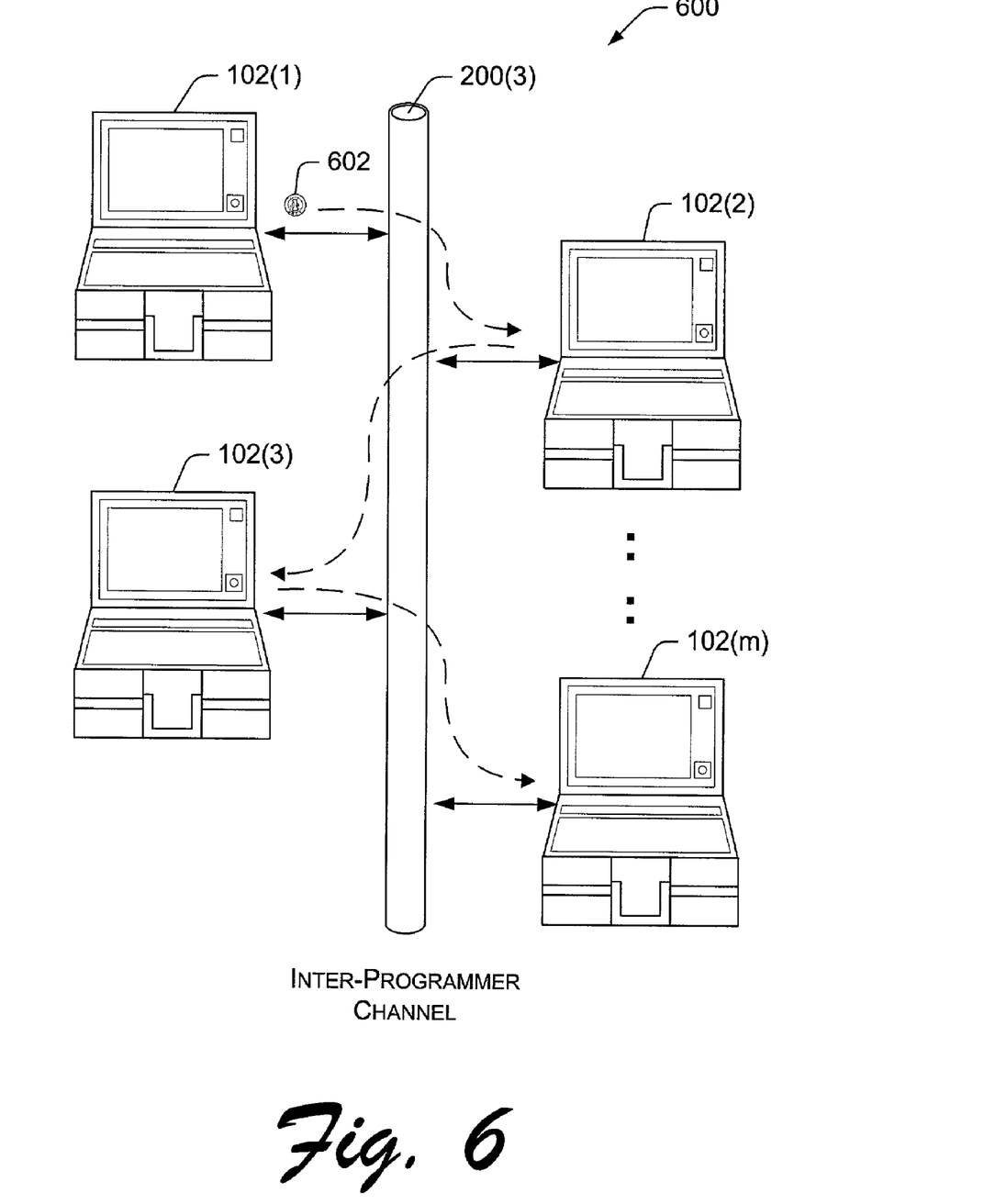
FIG. 6 illustrates an alternative inter-programmed communication protocol that coordinates programmer communication with the implantable devices.

FIG. 6 shows another possible inter-programmer communication protocol 600. Multiple programmers 102(1), 102 (2), . . . , 102(m) are illustrated within a viable telemetry range. The programmers 102(1)–102(m) communicate with each other via the inter-programmer channel 200(3) or via the back channel (not shown). According to this protocol, a communication token 602 is passed among the programmers 102(1)–102(m). The programmer that possesses the communication token 602 has the authority to communicate with a target implantable device. The other programmers do not have such authority, and instead wait until they possess the token 602.

When the token-possessing programmer finishes a communication exchange with the implantable device, the programmer passes the token onto another programmer. The token may be passed in a number of ways, such as sequentially from programmer to programmer, or on a requested basis where programmers who want to communicate over a device channel first submit a token request over the inter-programmer channel.

In addition to those described herein, other forms of coordination communication among multiple programmers may be used. For instance, programmers within a viable telemetry range may be pre-assigned a time slot in a time division multiplexing scheme.

Interference Alarm

Figure 7:
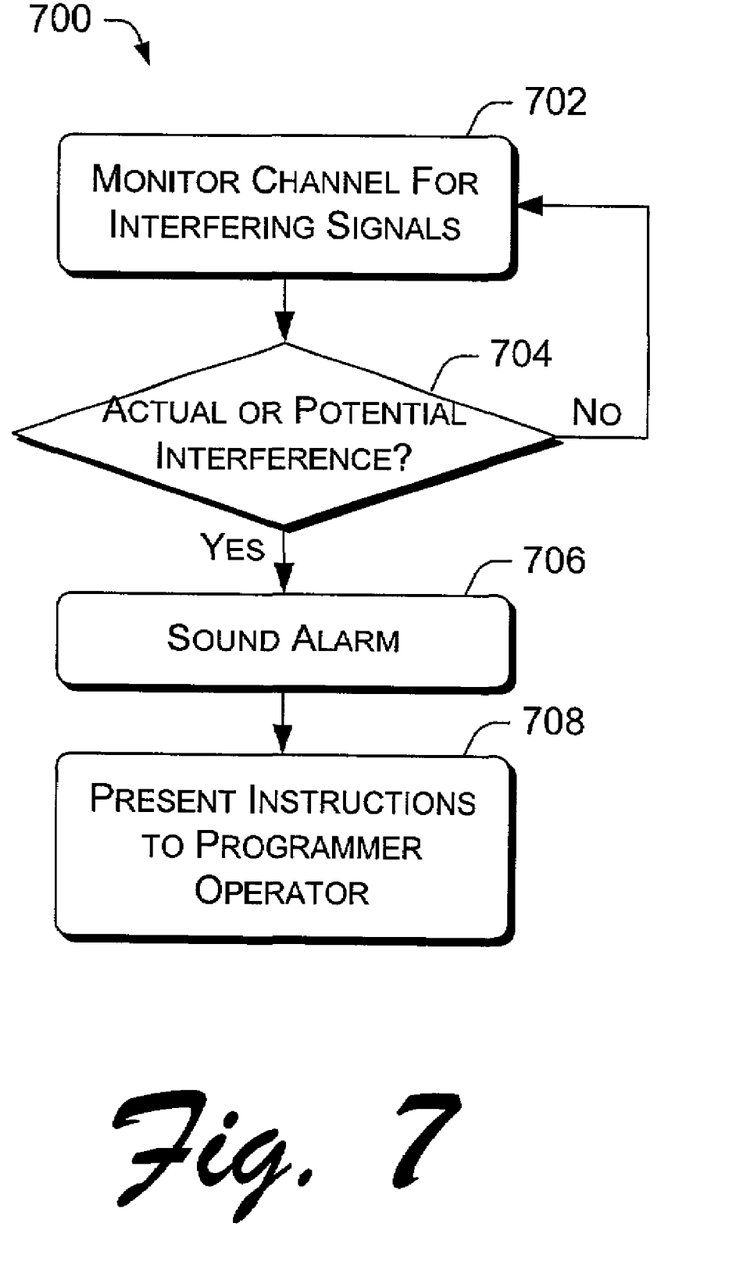
FIG. 7 illustrates a process for detecting interference and sounding an alarm in response.

FIG. 7 shows illustrates a process 700 for detecting interference and sounding an alarm in response. At block 702, the programmer monitors the communication channel for interfering signals. The communication channel may be a particular channel (e.g., a common frequency that all programmer share), or a group of channels that are used to support multi-channel communication. The monitoring is performed, for example, by the telemetry subsystem 330, and particularly the interference detector 334.

When signals are detected, the programmer determines whether the signals will, or potentially could, interfere with communication between the programmer and the device over the channel (block 704). This determination may be performed in a number of ways. For instance, the programmer may compare the signal strength against a threshold and deem signals exceeding the threshold as actual or potentially interfering signals. Another approach is to count errors and determine that there is interference when the error rate exceeds a given threshold. Where the programmer detects no such signals (i.e., the "no" branch from block 704), the programmer continues to monitor the channel).

If the detected signals are deemed interfering or at least pose a threat of interference (i.e., the "yes" branch from block 704), the programmer sounds alarm 326 to warn the programmer operator of the actual or potential interference (block 706). The alarm is designed to make a distinctive noise or rhythm that is immediately recognizable to the programmer operator. The programmer can also flash visual warning on the programmable display.

In addition to warning messages, the programmer can offer possible solutions. At block 708, the programmer may optionally present various instructions that inform the programmer operator what steps to take to ensure that the interference has not disrupted the communication with the implantable device. For instance, the instructions may direct the operator to move the telemetry antenna closer to the implantable device, or run cross-checks to make such that programming parameters were successfully transferred to the implantable device.

Exemplary Implantable Device

The implantable medical device may be implemented in any number of ways. Some monitor patient conditions while others dispense some form of therapy. Examples of possible devices include implantable nerve stimulators, implantable bio-monitoring device, implantable cardiac therapy devices, and so on. As noted above, the implantable medical device is illustrated as an implantable cardiac therapy device (ICTD).

Figure 8:
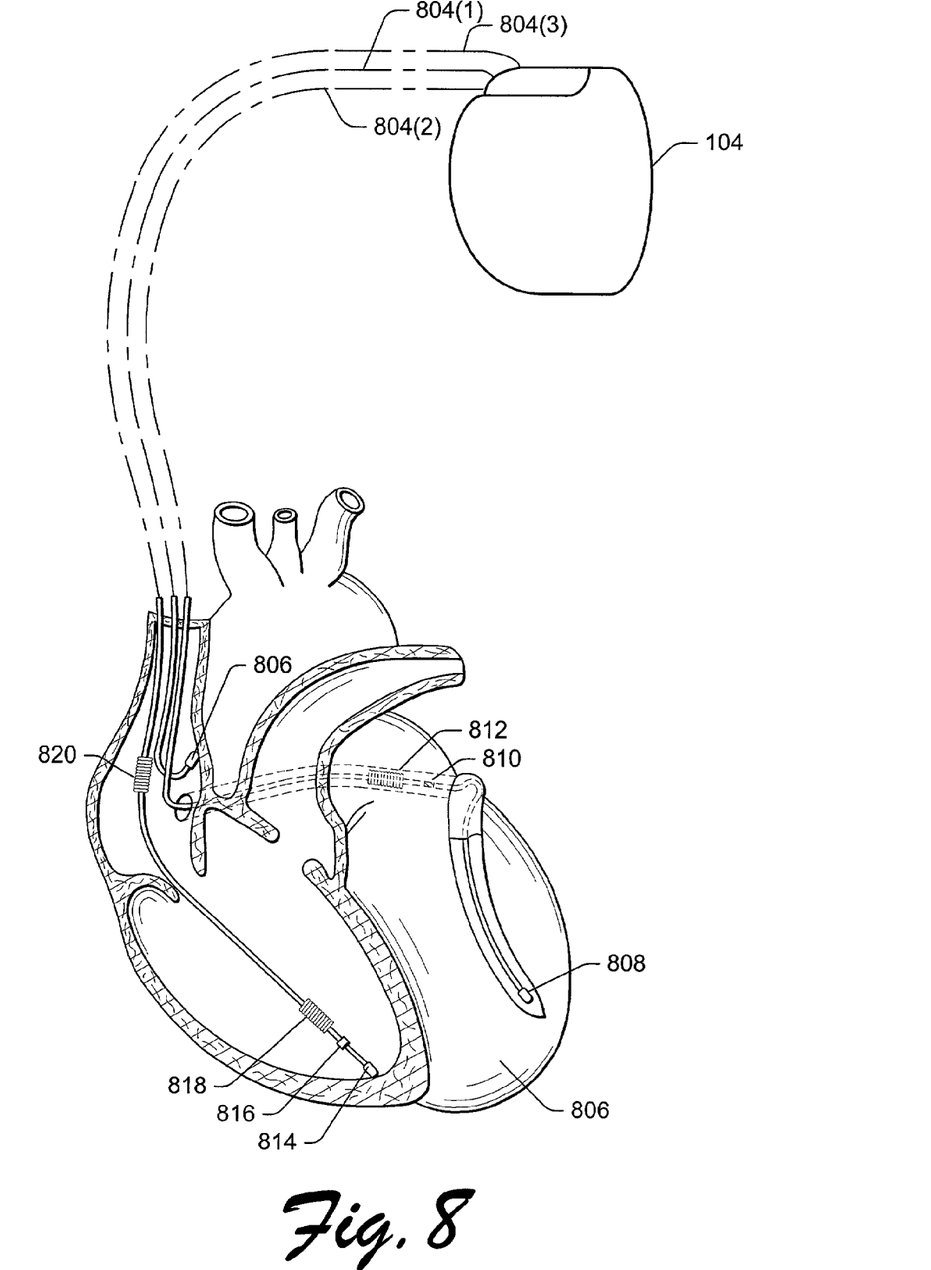
FIG. 8 is a simplified illustration for an implantable medical device in the form of an implantable cardiac therapy device.

FIG. 8 shows one exemplary ICTD 104 in electrical communication with a patient's heart 802 for monitoring heart activity and/or delivering stimulation therapy, such as pacing or defibrillation therapies. Three leads 804(1)–(3) interconnect the ICTD 104 with the patient's heart 806: a right atrial lead 804(1), a coronary sinus lead 804(2), and a right ventricular lead 804(3).

The right atrial lead 804(1) supports an atrial tip electrode 806, which typically is implanted in the patient's right atrial appendage. The coronary sinus lead 804(2) positions a left ventricular tip electrode 808 adjacent to the left ventricle and/or additional electrode(s) adjacent to the left atrium, such as a left atrial ring electrode 810 and a left atrial coil electrode 812. The right ventricular lead 804(3) is electrically coupled to a right ventricular tip electrode 814, a right ventricular ring electrode 816, a right ventricular (RV) coil electrode 818, and an SVC coil electrode 820.

Figure 9:
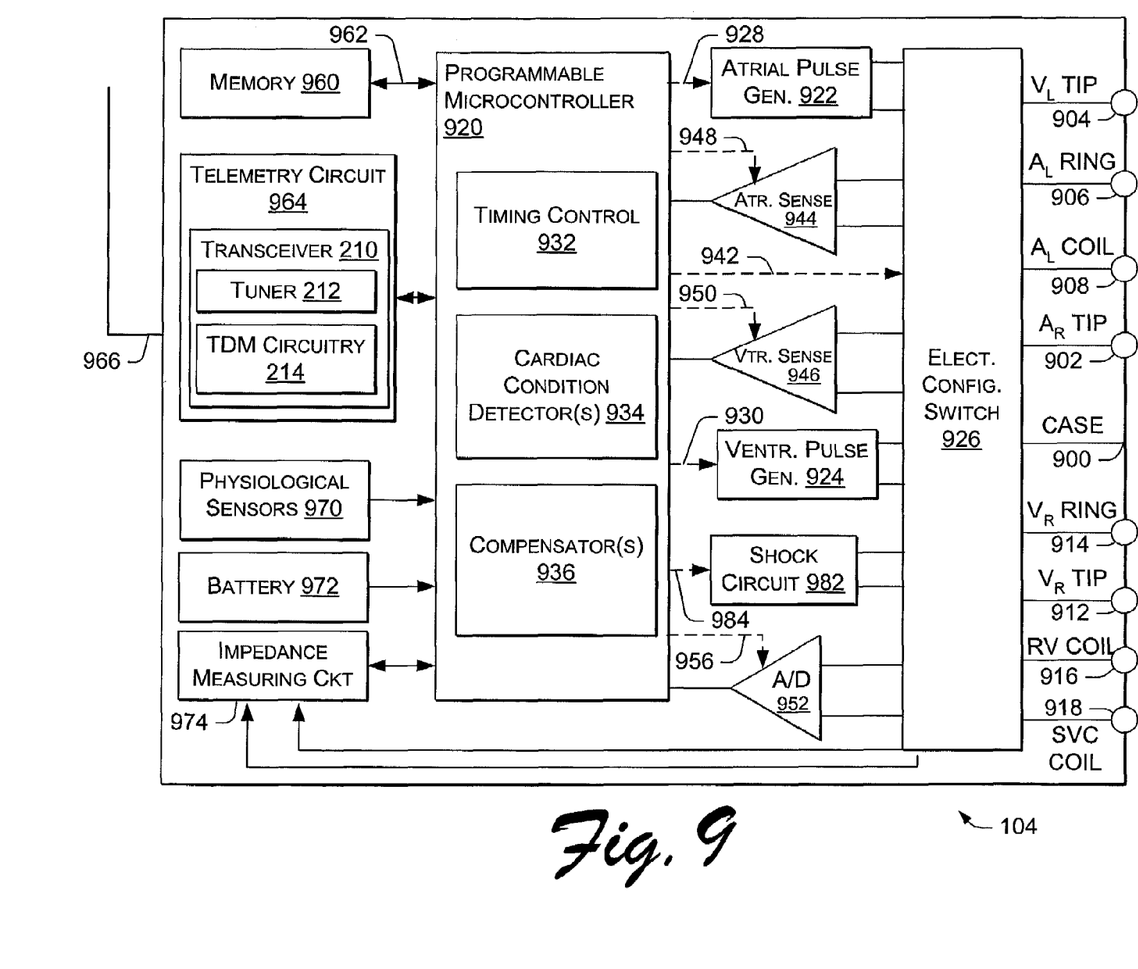
FIG. 9 is a functional block diagram of an exemplary implantable cardiac therapy device.

FIG. 9 shows an exemplary, simplified block diagram depicting various components of the ICTD 104. The components are housed in housing 900, which is often referred to as the "can", "case", "encasing", or "case electrode", and may be programmably selected to act as the return electrode for unipolar modes. Housing 900 further includes a connector (not shown) having a plurality of terminals (shown schematically and, for convenience, the names of the electrodes to which they are connected are shown next to the terminals), including:

a right atrial tip terminal ($A_R$ TIP) 902 for atrial tip electrode 806;

a left ventricular tip terminal ($V_L$ TIP) 904 for left ventricular tip electrode 808;

a left atrial ring terminal ($A_L$ RING) 906 for left atrial ring electrode 810;

a left atrial shocking terminal ($A_L$ COIL) 908 for left atrial coil electrode 812;

a right ventricular tip terminal ($V_R$ TIP) 912 for right ventricular tip electrode 814;

a right ventricular ring terminal ($V_R$ RING) 914 for right ventricular ring electrode 816;

a right ventricular shocking terminal (RV COIL) 916 for RV coil electrode 818; and an SVC shocking terminal (SVC COIL) 918 for SVC coil electrode 820.

The ICTD 104 includes a programmable microcontroller 920 that controls various operations of the ICTD, including cardiac monitoring and stimulation therapy. Microcontroller 920 includes a microprocessor (or equivalent control circuitry), RAM and/or ROM memory, logic and timing circuitry, state machine circuitry, and I/O circuitry. Microcontroller 920 is illustrated as including timing control circuitry 932 to control the timing of the stimulation pulses (e.g., pacing rate, atrio-ventricular (AV) delay, atrial interconduction (A—A) delay, or ventricular interconnection (V—V) delay, etc.) as well as to keep track of the timing of refractory periods, blanking intervals, noise detection windows, evoked response windows, alert individuals, marker channel timing, and so on.

Microcontroller 920 may further include various types of cardiac condition detectors 934 (e.g., an arrhythmia detector, a morphology detector, etc.) and various types of compensators 936 (e.g., orthostatic compensator, syncope response module, etc.). These components can be utilized by the device 104 for determining desirable times to administer various therapies. The components 932–936 may be implemented in hardware as part of the microcontroller 920, or as software/firmware instructions programmed into the device and executed on the microcontroller 920 during certain modes of operation.

The ICTD 104 further includes an atrial pulse generator 922 and a ventricular pulse generator 924 that generates pacing stimulation pulses for delivery by the right atrial lead 804(1), the coronary sinus lead 804(2), and/or the right ventricular lead 804(3) via an electrode configuration switch 926. It is understood that in order to provide stimulation therapy in each of the four chambers of the heart, the atrial and ventricular pulse generators, 922 and 924, may include dedicated, independent pulse generators, multiplexed pulse generators, or shared pulse generators. The pulse generators 922 and 924 are controlled by the microcontroller 920 via appropriate control signals 928 and 930, respectively, to trigger or inhibit the stimulation pulses.

The electronic configuration switch 926 includes a plurality of switches for connecting the desired electrodes to the appropriate I/O circuits, thereby providing complete electrode programmability. Accordingly, switch 926, in response to a control signal 942 from the microcontroller 920, determines the polarity of the stimulation pulses (e.g., unipolar, bipolar, combipolar, etc.) by selectively closing the appropriate combination of switches (not shown).

Atrial sensing circuits 944 and ventricular sensing circuits 946 may also be selectively coupled to the right atrial lead 804(1), coronary sinus lead 804(2), and the right ventricular lead 804(3), through the switch 926 to detect the presence of cardiac activity in each of the four chambers of the heart. Accordingly, the atrial and ventricular sensing circuits may include dedicated sense amplifiers, multiplexed amplifiers, or shared amplifiers. Switch 926 determines the "sensing polarity" of the cardiac signal by selectively closing the appropriate switches. In this way, the clinician may program the sensing polarity independent of the stimulation polarity.

The outputs of the atrial and ventricular sensing circuits are connected to the microcontroller 920 which, in turn, is able to trigger or inhibit the atrial and ventricular pulse generators 922 and 924, respectively, ion a demand fashion in response to the absence or presence of cardiac activity in the appropriate chambers of the heart. The sensing circuits 944 and 946 receive control signals over signal lines 948 and 950 from the microcontroller 920 for purposes of controlling the gain, threshold, polarization charge removal circuitry (not shown), and the timing of any blocking circuitry (not shown) coupled to the inputs of the sensing circuits 944 and 946.

Cardiac signals are also applied to inputs of an analog-to-digital (A/D) data acquisition system 952. The data acquisition system 952 is coupled to the leads 804(1)–(3) through the switch 926 to sample cardiac signals across any pair of desired electrodes. The data acquisition system 952 is configured to acquire intracardiac electrogram signals, convert the raw analog data into a digital signal, and store the digital signals for later processing and/or telemetric transmission to a programmer.

The microcontroller 920 is further coupled to a memory 960 by a suitable data/address bus 962. With memory 960, the ICTD 104 is able to sense and store a relatively large amount of data (e.g., from the data acquisition system 952), which may be exported to the programmer.

Operating parameters of the ICTD 104 may be non-invasively programmed into the memory 960 through a telemetry circuit 964 in telemetric communication with the programmer. The telemetry circuit 964 advantageously allows intracardiac electrograms and status information relating to the operation of the device 104 to be sent to the programmer. The telemetry circuit 964 further includes the transceiver 210, which is capable of communicating with the programmer at different frequency ranges, including, for example, high frequency ranges such as RF. A dedicated antenna 966, or leads 804, can be used as an antenna for the transceiver 210. The transceiver is shown as including a tuner 212 and/or TDM circuitry 214.

The ICTD 104 can further include one or more physiologic sensors 970, a battery 972, and impedance measuring circuit 974. Uses for an impedance measuring circuit 974 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 974 is advantageously coupled to the switch 926 so that any desired electrode may be used.

Conclusion

Although the invention has been described in language specific to structural features and/or methodological acts, it is to be understood that the subject matter defined in the appended claims is not necessarily limited to the specific features or acts described. Rather, the specific features and acts are disclosed as exemplary forms of implementing the claimed invention.

What is claimed is:

1. A system comprising:
   multiple programmers located within a viable telemetry range, each programmer being capable of communicating with an implantable medical device via one or more first communication channels within the viable telemetry range; and
   individual programmers being configured to communicate with one another on a second communication channel separate from the one or more first communication channels;
   wherein the first and second communication channels comprise different frequencies.

2. A system as recited in claim 1, wherein the first communications channels are supported by a wireless network and the second communication channel is supported by a wire-based network.

3. A system comprising:
   multiple programmers located within a viable telemetry range, each programmer being capable of communicating with an implantable medical device via one or more first communication channels within the viable telemetry range; and
   individual programmers being configured to communicate with one another on a second communication channel separate from the one or more first communication channels;
   wherein a particular programmer, prior to initiating communication with an implantable medical device, discovers which of the communication channels are available.

4. A system comprising:
   multiple programmers located within a viable telemetry range, each programmer being capable of communicating with an implantable medical device via one or more first communication channels within the viable telemetry range; and
   individual programmers being configured to communicate with one another on a second communication channel separate from the one or more first communication channels;
   wherein a particular programmer, prior to performing an operation with an implantable medical device, notifies other programmers of the operation.

5. A system as recited in claim 4, wherein the other programmers, in response to notification from the particular programmer, temporarily avoid communication with any implantable medical devices within the viable telemetry range.

6. A system comprising:
   multiple programmers located within a viable telemetry range, each programmer being capable of communicating with an implantable medical device via one or more first communication channels within the viable telemetry range; and
   individual programmers being configured to communicate with one another on a second communication channel separate from the one or more first communication channels;

wherein a particular programmer, following completion of communication with an implantable medical device over a particular communication channel, notifies other programmers that the particular communication channel is available.

7. A system comprising:
multiple programmers located within a viable telemetry range, each programmer being capable of communicating with an implantable medical device via one or more first communication channels within the viable telemetry range; and
individual programmers being configured to communicate with one another on a second communication channel separate from the one or more first communication channels;
wherein the individual programmers are each configured to detect interference from another programmer.

8. A system as recited in claim 7, wherein the multiple programmers coordinate with one another to manage communication between associated programmers and implantable medical devices.

9. A system comprising:
multiple programmers located within a viable telemetry range, each programmer being capable of communicating with an implantable medical device via one or more first communication channels within the viable telemetry range; and
individual programmers being configured to communicate with one another on a second communication channel separate from the one or more first communication channels;
wherein each programmer comprises:
an interference detector to detect interference from another programmer; and
an alarm to sound an audible warning when the interference is detected.

10. A system comprising:
multiple programmers located within a viable telemetry range, each programmer being capable of communicating with an implantable medical device via one or more communication channels within the viable telemetry range; and
individual programmers being configured to communicate with one another to manage communication between associated programmers and implantable medical devices within the viable telemetry range;
wherein the programmers coordinate with one another over a back channel independent of the one or more communication channels.

11. A system as recited in claim 10, wherein the programmers coordinate with one another over one of the one or more communication channels.

12. A system comprising:
multiple programmers located within a viable telemetry range, each programmer being capable of communicating with an implantable medical device via one or more communication channels within the viable telemetry range; and
individual programmers being configured to coordinate with one another to manage communication between associated programmers and implantable medical devices within the viable telemetry range;
wherein the programmers coordinate with one another by a token protocol in which a token is passed among the programmers such that a programmer that possesses the token is authorized to communicate.

13. A system comprising:
multiple programmers located within a viable telemetry range, each programmer being capable of communicating with an implantable medical device via one or more communication channels within the viable telemetry range; and
individual programmers being configured to coordinate with one another to manage communication between associated programmers and implantable medical devices within the viable telemetry range;
wherein a particular programmer, prior to initiating communication with an implantable medical device, interrogates other programmers to discover which of the communication channels are available.

14. A system comprising:
multiple programmers located within a viable telemetry range, each programmer being capable of communicating with an implantable medical device via one or more communication channels within the viable telemetry range; and
individual programmers being configured to coordinate with one another to manage communication between associated programmers and implantable medical devices within the viable telemetry range;
wherein a particular programmer, prior to performing an operation with an implantable medical device, notifies other programmers of the operation.

15. A system as recited in claim 14, wherein the other programmers, in response to notification from the particular programmer, temporarily halt communication with any implantable medical devices in the viable telemetry range.

16. A system comprising:
multiple programmers located within a viable telemetry range, each programmer being capable of communicating with an implantable medical device via one or more communication channels within the viable telemetry range; and
individual programmers being configured to coordinate with one another to manage communication between associated programmers and implantable medical devices within the viable telemetry range;
wherein a particular programmer, following completion of communication with an implantable medical device over a particular communication channel, notifies other programmers that the particular communication channel is available.

17. A system comprising:
multiple programmers located within a viable telemetry range, each programmer being capable of communicating with an implantable medical device via one or more communication channels within the viable telemetry range; and
individual programmers being configured to coordinate with one another to manage communication between associated programmers and implantable medical devices within the viable telemetry range;
wherein the individual programmers are each configured to detect interference from another programmer.

18. A system comprising:
multiple programmers located within a viable telemetry range, each programmer being capable of communicating with an implantable medical device via one or more communication channels within the viable telemetry range; and
individual programmers being configured to coordinate with one another to manage communication between associated programmers and implantable medical devices within the viable telemetry range;
wherein each programmer comprises:
an interference detector to detect interference from another programmer; and
an alarm to sound an audible warning when the interference is detected.

19. A system comprising:
first and second programmers located within a viable telemetry range; and
the first programmer being configured to discover and select an available communication channel for communicating with an implantable medical device within the viable telemetry range and to inform the second programmer of the selected communication channel.

20. A system as recited in claim 19, wherein the first programmer discovers available communication channels by requesting the second programmer to identify any communication channels being used.

21. A system as recited in claim 19, wherein the second programmer, in response to being informed of the selected communication channel, marks the selected communication channel as being reserved.

22. A system as recited in claim 19, wherein the first programmer, following completion of communication with the implantable medical device, notifies the second programmer that the selected channel is available.

23. A system as recited in claim 19, wherein the first programmer is further configured to notify the second programmer of an upcoming operation involving communication from the first programmer to the implantable medical device.

24. A system as recited in claim 23, wherein the second programmer, in response to notification, is configured to temporarily halt communication with any implantable medical devices.

25. A programmer for an implantable medical device, comprising:
a memory;
a processor operatively coupled to the memory; and
a telemetry subsystem coupled to the processor, the telemetry subsystem being configured to transmit and receive signals over one or more first communication channels to enable communication with an implantable medical device and to transmit and receive signals over a second communication channel to enable communication with another programmer;
wherein the first and second communication channels comprise different frequencies.

26. A programmer as recited in claim 25, wherein the one or more first communication channels are supported by a wireless connection and the second communication channel is supported by a wired connection.

27. A programmer for an implantable medical device, comprising:
a memory;
a processor operatively coupled to the memory;
a telemetry subsystem coupled to the processor, the telemetry subsystem being configured to transmit and receive signals over one or more first communication channels to enable communication with an implantable medical device and to transmit and receive signals over a second communication channel to enable communication with another programmer; and
a channel table stored in the memory, the channel table tracking which of the first communication channels are in use and/or available for use.

28. A programmer for an implantable medical device, comprising:
a memory;
a processor operatively coupled to the memory;
a telemetry subsystem coupled to the processor, the telemetry subsystem being configured to transmit and receive signals over one or more first communication channels to enable communication with an implantable medical device and to transmit and receive signals over a second communication channel to enable communication with another programmer; and
an interference detector to detect actual and/or potential interference from another programmer.

29. A programmer as recited in claim 28, further comprising a warning mechanism that is activated when the interference detector detects the interference.

30. A programmer for an implantable medical device, comprising:
programming means for programming the implantable medical device; and
inter-programmer communication means for communicating with other programmers to coordinate communication between associated programmers and implantable medical devices so that only one programmer is communicating with one implantable medical device within a viable communication range at any given time.

31. A programmer as recited in claim 30, wherein the inter-programmer communication means comprises transceiver means for transmitting and receiving signals over a frequency that is different from one or more frequencies used by the programming means for programming the implantable medical device.

32. A programmer as recited in claim 30, wherein the inter-programmer communication means comprises interrogation means for discovering communication channels that are available for use in communicating with implantable medical devices.

33. A programmer as recited in claim 30, wherein the inter-programmer communication means comprises notification means for notifying the other programmers of an impending programming operation when programming the implantable medical device.

34. A programmer as recited in claim 30, wherein the inter-programmer communication notification means comprises means for notifying other programmers that a communication channel used to program the implantable medical device is available.

35. A programmer as recited in claim 30, further comprising interference detection means for detecting interference from another programmer.

36. A method comprising:
communicating between programmers and implantable medical devices over one or more first channels; and
communicating among the programmers over a second channel that is different from the one or more first channels;
wherein the first and second channels comprise different frequencies.

37. A method as recited in claim 36, wherein the one or more first channels are supported by a wireless connection and the second channel is supported by a wired connection.

38. A method comprising:
communicating between programmers and implantable medical devices over one or more communication channels within a viable telemetry range; and
coordinating, among the programmers, communications between the programmers and the implantable medical devices so that only one programmer is communicating with one implantable medical device within the viable telemetry range at any given time.

39. A method as recited in claim 38, wherein the coordinating comprises communicating among the programmers over one of the communication channels.

40. A method as recited in claim 38, wherein the coordinating comprises communicating among the programmers over a back channel independent of the one or more communication channels.

41. A method as recited in claim 38, wherein the coordinating comprises passing a token among the programmers so that a programmer that possesses the token is authorized to initiate communication.

42. A method of operating a programmer of an implantable medical device, comprising:

communicating with one or more other programmers to identify available communication channels that may be used to communicate with an implantable medical device;

selecting a communication channel from among the available channels; and informing the other programmers of the selected communication channel.

43. A method as recited in claim 42, further comprising communicating with one or more other programmers to inform the programmers of an upcoming operation involving communication with an implantable medical device.

44. A method as recited in claim 42, further comprising informing the other programmers when the selected communication channel is once again available for use.

45. A method for operating a programmer of an implantable medical device, comprising:

receiving a notice from another programmer that the other programmer is preparing to communicate with an implantable medical device within a viable telemetry range; and temporarily halting communication within the viable telemetry range.

* * * * *